(12) United States Patent
Safai et al.

(10) Patent No.: US 9,546,004 B1
(45) Date of Patent: Jan. 17, 2017

(54) WATER AND ICE DETECTION AND QUANTITATIVE ASSESSMENT SYSTEM FOR INGRESSION PRONE AREAS IN AN AIRCRAFT

(71) Applicant: The Boeing Company, Seal Beach, CA (US)

(72) Inventors: Morteza Safai, Newcastle, WA (US); Kimberly D. Meredith, Newcastle, WA (US); Sahrudine Apdalhaliem, Seattle, WA (US)

(73) Assignee: THE BOEING COMPANY, Chicago, IL (US)

( * ) Notice: Subject to any disclaimer, the term of this patent is extended or adjusted under 35 U.S.C. 154(b) by 270 days.

(21) Appl. No.: 14/216,397

(22) Filed: Mar. 17, 2014

(51) Int. Cl.
*B64D 45/00* (2006.01)
*G01N 27/02* (2006.01)

(52) U.S. Cl.
CPC ............... *B64D 45/00* (2013.01); *G01N 27/02* (2013.01)

(58) Field of Classification Search
CPC ................................ G01N 27/02; B64D 45/00
See application file for complete search history.

(56) References Cited

U.S. PATENT DOCUMENTS

| | | | |
|---|---|---|---|
| 2004/0206854 A1* | 10/2004 | Shah ...................... | B64D 15/20 244/144 |
| 2005/0016278 A1* | 1/2005 | Knowles ................ | B64D 15/20 73/592 |
| 2007/0216536 A1* | 9/2007 | Alfano ................... | G08B 19/02 340/583 |

* cited by examiner

*Primary Examiner* — Jermele M Hollington
*Assistant Examiner* — Haidong Zhang
(74) *Attorney, Agent, or Firm* — Francisco A. Rubio-Campos; The Boeing Company

(57) ABSTRACT

A water and ice detection and quantitative assessment system ("WIDQAS") for moisture detection and assessment of water accumulation on an aircraft having an airframe that has at least one enclosed space within the airframe is described. The WIDQAS may include a plurality of sensors and a data measurement device. The plurality of sensors may be arranged in the at least one enclosed space within the airframe and each sensor of the plurality of sensors may be configured to detect a presence of moisture in the at least one enclosed space and generate a data measurement that is responsive to the detection of moisture in the at least one enclosed space. The data measurement device is in signal communication with the plurality of sensors and may be configured to record the data measurement for each sensor and record identifying information about the measurement during a flight of the aircraft.

20 Claims, 8 Drawing Sheets

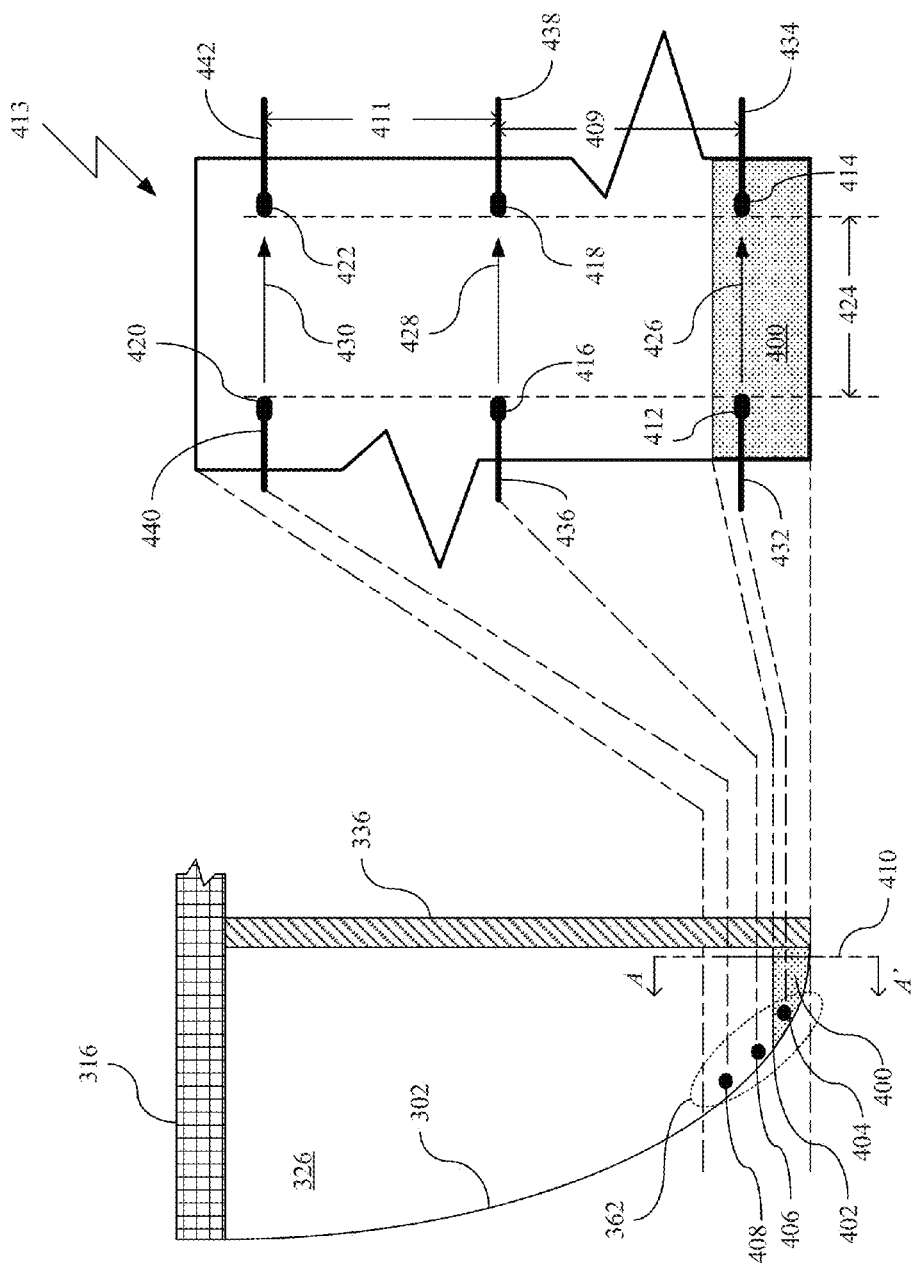

WATER AND ICE DETECTION AND QUANTITATIVE ASSESSMENT SYSTEM FOR INGRESSION PRONE AREAS IN AN AIRCRAFT

BACKGROUND OF THE INVENTION

1. Field of the Invention

The present invention relates generally to systems and methods for detecting moisture ingress, and more particularly, to systems and methods for detecting water and ice accumulation on an aircraft.

2. Related Art

The use of air travel has greatly increased in recent decades to the point that it is today a common form of transportation. As such, there is an ever present need to increase the safety, efficiency, and environmental impact of modern aircraft.

Generally, transport type commercial, military, and some private aircraft fly through environmentally hostile environments that typically lead to water accumulation in these types of aircraft. Specifically, transport carrying aircraft typically have moisture-related problems that include ice formation within the airframe of the aircraft, water dripping onto passengers within the passenger cabin, water accumulation in the airframe, electrical equipment failures, and wet insulation blankets within the airframe of the aircraft. Generally, the extent of these problems will vary among aircraft operators and among individual aircraft depending on how they are utilized; however, even taking these factors into account, all transport aircraft will experience some type of moisture-related problems.

Specifically, all commercial aircraft that carry passengers will experience moisture-related problems in service because the chief source of moisture inside these aircraft is passenger respiration and the resulting condensation (or freezing) of this moisture on the skin of the aircraft. Additionally, there may be water ingress (i.e., moisture from the external environment of the aircraft) into the aircraft while the aircraft is on the ground before takeoff. This combined moisture (i.e., from both respiration and water ingress) may condense along the airframe while the aircraft is in flight.

Typically, this type of condensation on the airframe of an aircraft occurs during flight when the temperature of both the outside air and the airframe are very cold. It is appreciated by those skilled in the art that the atmospheric air temperature drops relative to geometric altitude. Specifically, Tables 1 and 2 provide the highest and lowest temperature ever recorded as function of geometric altitude based on MIL-HDBK-310 (from the Military Handbook: Global Climatic Data For Developing Military Products (23 Jun. 1997)). The airplane is operating within this environment envelope. Depending on airplane model, the temperature at the skin of the airplane is varied and it is greatly dependent on operational altitude and cruising speed.

TABLE 1

Highest Recorded Temperature as a Function of Geometric Altitude

| GEOMETRIC ALTITUDE | | | | | | PRESSURE ALT. | |
|---|---|---|---|---|---|---|---|
| ALTITUDE | | TEMP | | DENSITY | | TEMP | |
| (km) | (kft) | (° C.) | (° F.) | (kg/m$^3$) | (lb/ft$^3$) | (° C.) | (° F.) |
| 0 | 0 | 58 | 136 | 1052 × 10$^{-3}$ | 657 × 10$^{-4}$ | — | — |
| 1 | 3.28 | 41 | 106 | 1018 | 636 | 40 | 104 |
| 2 | 6.56 | 32 | 90 | 916 | 572 | 31 | 88 |
| 4 | 13.1 | 19 | 66 | 762 | 476 | 19 | 66 |
| 6 | 19.7 | 8 | 46 | 611 | 381 | 6 | 43 |
| 8 | 26.2 | −4 | 25 | 499 | 312 | −4 | 25 |
| 10 | 32.8 | −13 | 9 | 393 | 245 | −18 | 0 |
| 12 | 39.4 | −22 | −8 | 316 | 197 | −27 | −17 |
| 14 | 45.9 | −30 | −22 | 208 | 130 | −34 | −29 |
| 16 | 52.5 | −35 | −31 | 156 | 97 | −35 | −31 |
| 18 | 59.1 | −35 | −31 | 118 | 74 | −34 | −29 |
| 20 | 65.6 | −31 | −24 | 86 | 54 | −31 | −24 |
| 22 | 72.2 | −29 | −20 | 64 | 40 | −31 | −24 |
| 24 | 78.7 | −33 | −27 | 48 | 30 | −31 | −24 |
| 20 | 85.3 | −27 | −17 | 36 | 22 | −27 | −17 |
| 28 | 91.9 | −22 | −8 | 27 | 17 | −22 | −8 |
| 30 | 98.4 | −17 | 1 | 20 | 12 | −17 | 0 |

TABLE 2

Lowest Recorded Temperature as a Function of Geometric Altitude

| GEOMETRIC ALTITUDE | | | | | | PRESSURE ALT. | |
|---|---|---|---|---|---|---|---|
| ALTITUDE | | TEMP | | DENSITY | | TEMP | |
| (km) | (kft) | (° C.) | (° F.) | (kg/m$^3$) | (lb/ft$^3$) | (° C.) | (° F.) |
| 0 | 0 | −68 | −90 | 1780 × 10$^{-3}$ | 1111 × 10$^{-4}$ | — | — |
| 1 | 3.28 | −54 | −65 | 1419 | 886 | −56 | −69 |
| 2 | 6.56 | −47 | −53 | 1147 | 716 | −47 | −53 |
| 4 | 13.1 | −53 | −63 | 899 | 561 | −51 | −60 |
| 6 | 19.7 | −61 | −78 | 681 | 425 | −60 | −76 |
| 8 | 26.2 | −68 | −90 | 510 | 318 | −64 | −83 |
| 10 | 32.8 | −75 | −103 | 409 | 255 | −73 | −99 |
| 12 | 39.4 | −80 | −112 | 314 | 196 | −77 | −107 |
| 14 | 45.9 | −77 | −107 | 218 | 136 | −78 | −108 |
| 16 | 52.5 | −87 | −125 | 208 | 130 | −87 | −125 |
| 18 | 59.1 | −88 | −126 | 143 | 89 | −85 | −121 |
| 20 | 65.6 | −87 | −125 | 78 | 49 | −83 | −117 |
| 22 | 72.2 | −85 | −121 | 54 | 34 | −85 | −121 |
| 24 | 78.7 | −86 | −123 | 38 | 24 | −85 | −121 |
| 20 | 85.3 | −84 | −119 | 29 | 18 | −85 | −121 |
| 28 | 91.9 | −84 | −119 | 20 | 12 | −85 | −121 |
| 30 | 98.4 | −85 | −121 | 11 | 6.9 | −85 | −121 |

As such, the airframe temperatures are usually below the dew point of the air in the passenger cabin of the aircraft, causing some amount of condensation to form during most flights from the water vapor in the moist air inside the aircraft. This condensation results when the moist air in the passenger cabin moves to the cold airframe. The cabin air passes through small gaps in the insulation coverage between the inner surfaces of the airframe and outer skin of the airframe and then cools rapidly when it comes in contact with the inside surface of the outer skin of the airframe.

Buoyancy forces typically induce a continuous flow of air and continuous movement of moisture to the cold airframe. Usually, the rate of condensation depends on the rate of buoyancy-driven air movement to the airframe as well as the cabin humidity level. The in-flight cabin humidity levels are low from a standpoint of human comfort (i.e., usually less than 20 percent relative humidity); however, the cabin air is not completely dry, and any moisture it contains will condense as the cabin air moves over the cold airframe. In addition, because the airframe temperatures in flight are normally below the freezing point of water, most of the condensed water vapor from the cabin air will freeze to form ice in the form of frost, which typically accumulates along some of the inner surfaces of the airframe such as, for example, the inside surface of the outer skin of the airframe.

Once the aircraft descends and finally lands, the frost or ice melts rapidly if the conditions allow the aircraft skin temperature to rise above freezing. This typically causes a sudden onset of drainage fluid as the ice melts, which, if not managed completely, drips into the crown area (i.e., the attic) of the aircraft (and possibly into the passenger cabin), and other enclosed spaces of the airframe. Once condensed and unfrozen, the liquid water accumulates within the airframe in different enclosed spaces or in the insulation blankets used to insulate the inner surfaces of the airframe from the outer skin. This process may repeat itself many times as the aircraft travels back and forth between destinations resulting in cyclic loading to the airframe structure and/or various electrical systems in the aircraft.

In general, these condensation conditions and the resulting moisture problems are influenced heavily by seating density and aircraft operations, especially load factors and utilization rates. High passenger loads result in higher cabin humidity and higher condensation rates. High aircraft-utilization rates result in more time during which the airframe is below the dew point or frost point and greater accumulations of frost and water on a daily basis. Generally, some of the most severe moisture problems occur on aircraft with combinations of high seating density, high load factors, and high utilization rates.

In order to better illustrate the above discussion, in FIG. 1, a front cross-sectional view of a known aircraft 100 is shown. The aircraft 100 is shown to have an airframe structure that includes a fuselage 102 and a pair of wings 104. The fuselage 102 includes an outer fuselage skin 106, an inner fuselage skin 108 (which may also be referred to as an inner fuselage sidewall 108), and a door 110. Insulation blanket material 112 is located between the outer fuselage skin 106 and the inner fuselage skin 108. The outer fuselage skin 106 is in contact with the outside environment 114 and the inner fuselage skin 108 is in contact with the inside environment 116. The inside environment 116 includes a plurality of passenger seats 118 located within a passenger cabin.

When water vapor 120 enters the inside environment 116 of the aircraft via water ingress from outside the door 110 or from respiration of passengers sitting in the passenger seats 118, it typically travels along different parts of the inside environment 116 and comes in contact with the inner fuselage skin 108. Assuming that there is an insulation blanket material 112 located between the outer fuselage skin 106 and the inner fuselage skin 108, the water vapor 120 typically passes through the inner fuselage skin 108 and insulation blanket material 112 to the outer fuselage skin 106.

Unfortunately, when the aircraft is in flight at a high enough altitude and the water vapor 120 comes in contact with the outer fuselage skin 106, the water vapor 118 will immediately condense into water that may freeze into ice 122 (i.e., frost) on the inside of the outer fuselage skin 106. Once the aircraft descends to a low enough altitude and/or lands, the ice 122 may melt and drain 124 along the inside of the outer fuselage skin 106 to form an accumulation of water 126 somewhat along the inside of the outer fuselage skin 106. Similarly, some of water vapor 120 may not actually freeze into ice and will simply condense into liquid water that will also drain 124 along the inside of the outer fuselage skin 106 to add to the accumulation of water 126. It is appreciated that as some of the liquid water drains 124 along the inside of the outer fuselage skin 106 it will be absorbed (not shown) by the insulation blanket material 112.

It is appreciated the path of drainage 124 is an example path and that draining water may take multiple paths throughout the airframe 100 to reach the pool of accumulated water 126. As another example, the melted water from the ice 122 may drain 128 to the pool of accumulated water 126 through part of insulating blanket material 112 inside of the outer fuselage skin 106 until it reaches the floor board 130 of the passenger cabin. Once it reaches the cabin floor board 130, it may drain 128 along the cabin floor board 130 until it finds an opening in the cabin floor board 130 where it then drips 134 to the pool of accumulated water 126.

If the insulation blanket material 112 is faulty because it has absorbed enough water so that it no longer functions properly in thermally insulating the outer fuselage skin 106 from the inner fuselage skin 108, such that the inner fuselage skin 108 is maintained at a below freezing temperature, the water vapor 118 may also freeze along the inner fuselage skin 108 and consequently form ice accumulation (i.e., frost) and accumulation of water (not shown) along the inner fuselage skin 108 similar to the ice 120 accumulation along the inside of the outer fuselage skin 106 and accumulation of water 124 somewhat along the inside of the outer fuselage skin 106.

This accumulation of ice and water typically leads to damage of the aircraft structure and/or systems, increased weight of the aircraft (caused by the increased water weight), and discomfort of the passengers within the aircraft. Specifically, ice accumulation within the aircraft structure may cause problems or even failure to mechanical movement of mechanical systems such as, on the less dangerous side, a roller shade assembly of a window shade, possible breakdown of the insulation material between the outer and inner fuselage skin of the aircraft, to problems with the landing gear or control surfaces of the aircraft. Water accumulation within the aircraft structure may cause problems that include increased humidity and possible water leakage (i.e., dripping) within the passenger compartment of the aircraft leading to passenger discomfort and reduced passenger satisfaction within the aircraft, increased weight of the aircraft (which leads to greater fuel consumption), accumulation of water in the cargo bay area of the aircraft, accumulation of water in the air conditioning ducts within the aircraft, corrosion of parts of the aircraft structure, corrosion and subsequent failure of electrical wiring within the aircraft, and short circuitry of onboard electrical system. As such, there is a need for a system and method for detecting and quantitatively assessing any water ingress and accumulation of ice and water in an aircraft.

SUMMARY

A water and ice detection and quantitative assessment system ("WIDQAS") for moisture detection and assessment of water accumulation on an aircraft having an airframe that has at least one enclosed space within the airframe is described. The WIDQAS may include a plurality of sensors and a data measurement device. The plurality of sensors may be arranged in the at least one enclosed space within the airframe and each sensor of the plurality of sensors may be configured to detect a presence of moisture in the at least one enclosed space and generate a data measurement that is responsive to the detection of moisture in the at least one enclosed space. The data measurement device is in signal communication with the plurality of sensors and may be configured to record the data measurement for each sensor and record identifying information about the measurement during a flight of the aircraft.

In an example of operation, the WIDQAS may perform a method including monitoring the plurality of sensors for the presence of water and receiving a data measurement indicating the presence of water at a sensor of the plurality of sensors. The method also includes recording identifying information related to the sensor and retrieving data from a lookup table ("LUT"), wherein the LUT data is related to the sensor. Moreover, the method further includes determining a notification level for the received data measurement from the sensor using the LUT data and storing the received data measurement with the corresponding identifying information on a storage device.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE FIGURES

The invention may be better understood by referring to the following figures. The components in the figures are not necessarily to scale, emphasis instead being placed upon illustrating the principles of the invention. In the figures, like reference numerals designate corresponding parts throughout the different views.

FIG. 4A is a front cross-sectional view of a cut-away portion of an enclosed space shown in FIG. 3 utilizing an example of an implementation of the WIDQAS in accordance with the present invention.

FIG. 4B is a side cross-sectional view of an enlarged portion of the cut-away portion of the enclosed space shown in FIGS. 3 and 4A utilizing an example of an implementation of the WIDQAS in accordance with the present invention.

DETAILED DESCRIPTION

A water and ice detection and quantitative assessment system ("WIDQAS") for moisture detection and assessment of water accumulation on an aircraft having an airframe that has at least one enclosed space within the airframe is described. The WIDQAS may include a plurality of sensors and a data measurement device. The plurality of sensors may be arranged in the at least one enclosed space within the airframe and each sensor of the plurality of sensors may be configured to detect a presence of moisture in the at least one enclosed space and generate a data measurement that is responsive to the detection of moisture in the at least one enclosed space. The data measurement device is in signal communication with the plurality of sensors and may be configured to record the data measurement for each sensor and record identifying information about the measurement during a flight of the aircraft.

Figure 1:
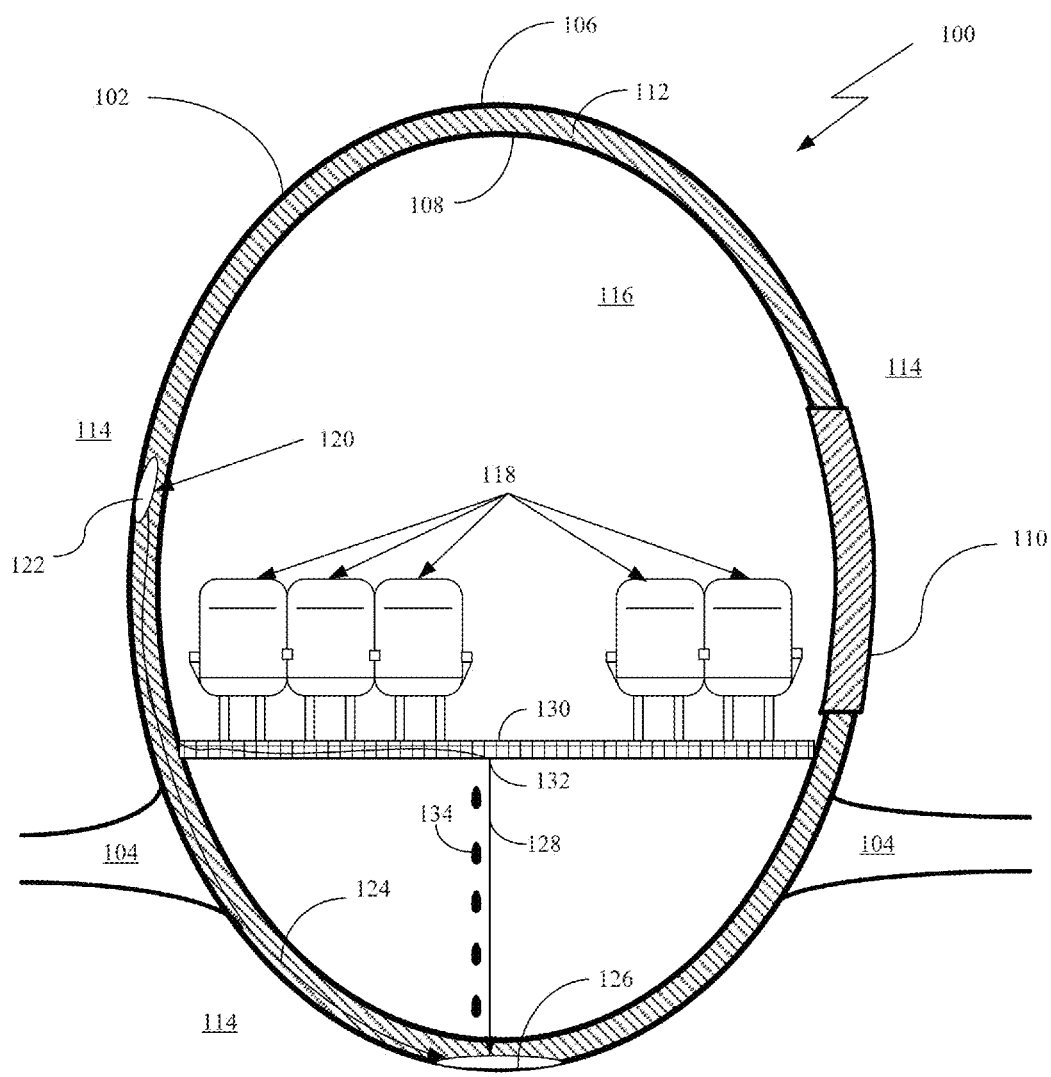
FIG. 1 is a front cross-sectional view of a known fuselage of an airframe of an aircraft.
Figure 2:
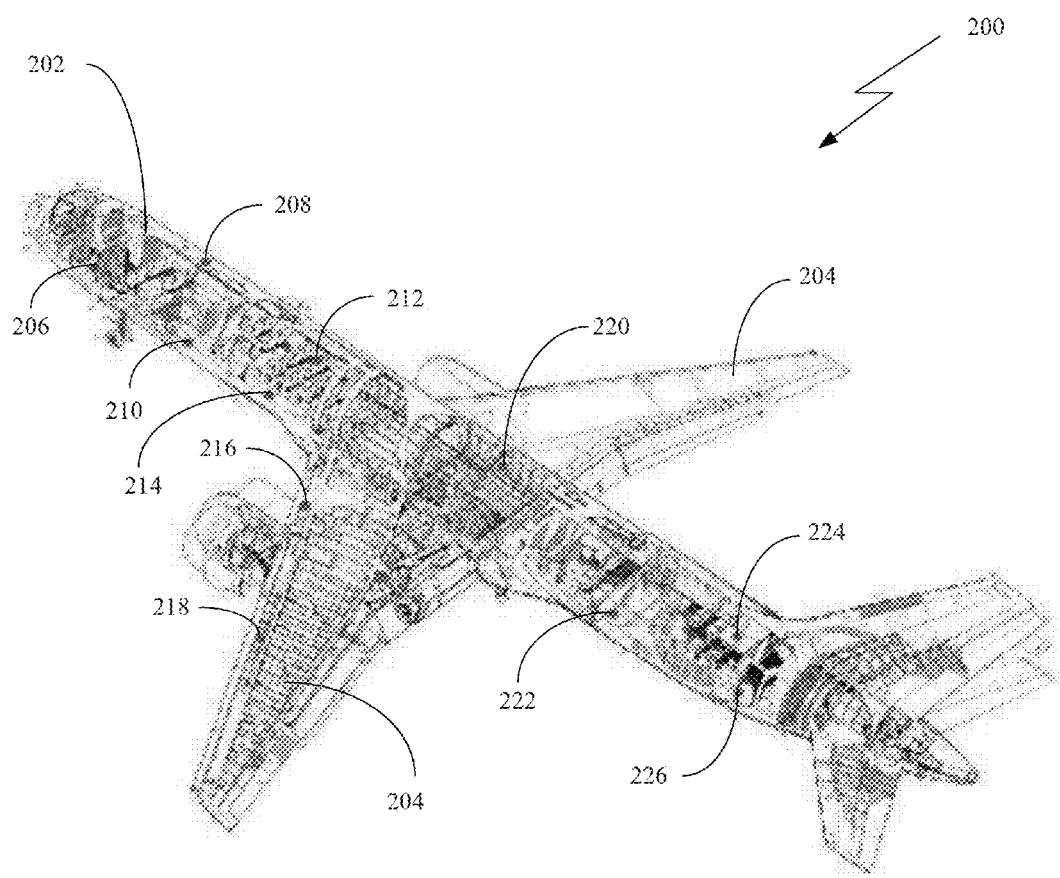
FIG. 2 is a back prospective view of an example of an implementation of an aircraft utilizing a water and ice detection and quantitative assessment system ("WIDQAS") in accordance with the present invention.

In FIG. 2, a rear perspective view of an example of an implementation of an aircraft 200 utilizing the WIDQAS in accordance with the present invention is shown. The aircraft 200 has an airframe structure that includes a fuselage 202 and a pair of wings 204. For most of its length, the fuselage 202 has an elliptical cross section and is of a semi-monocoque (i.e., stressed skin) design having an outer airframe skin (herein referred to as an outer fuselage skin) supported on an inner fuselage peripheral frame. The pair of wings 204 are also of a semi-monocoque design having an airframe skin (generally known as the wing surface) and an inner wing peripheral frame.

In this example, the aircraft 200 may have a plurality of sensors (sensors 206, 208, 210, 212, 214, 216, 218, 220, 222, 224, and 226) configured to detect the presence of moisture (including both water vapor and water in a liquid state), non-water liquid, or ice (both frozen water or frozen non-water). The plurality of sensors (sensors 206, 208, 210, 212, 214, 216, 218, 220, 222, 224, and 226) may include passive environmental sensors such as, for example, humidity, conductivity sensors, or both, that may be located along different parts of the structure of the aircraft 200 so as to measure the presence and accumulation of moisture, non-water liquid, or ice at the positions where the individual sensors are located. The sensors may be distributed throughout the airframe at water ingress prone areas (i.e., between interior panels and the exterior skin of the airframe, particularly near doors and windows, environmental control system ("ECS") ducts, in a lower lobe of the airframe where electronics may often be located).

The sensors may be wired, or wireless, and are in signal communication with one or more data measurement devices (not shown) within (i.e., on-board) the aircraft 200 via a plurality of signal paths along the airframe of the aircraft 200. Each data measurement device may be configured to receive measurements from a sub-plurality of the plurality of sensors (sensors 206, 208, 210, 212, 214, 216, 218, 220, 222, 224, and 226). Additionally, the measurements may be collected in real-time or over the duration of a flight. Moreover, additional information may be collected and stored by the data measurement devices with each actual measurement. Examples of this additional information may include a time stamp, temperature, and other pertinent information that may be utilized to map the water accumulation and transition of water to ice during a given flight. The data collected may be utilized to map the presence of water at various times in the various monitored locations in the aircraft 200.

As an example, the data measurement device may be a data recorder, such as, for example, a multi-channel analyzer, or a processor-based on-board system. The data collected by the plurality of sensors (sensors 206, 208, 210, 212, 214, 216, 218, 220, 222, 224, and 226) may be utilized to develop a profile of water accumulation within the aircraft 200. The resulting profile of water accumulation within the aircraft 200 may then be utilized to identify corrective actions that may be taken to prevent the reoccurrence (or at least reduce the effect) of the water ingress and accumulation problem.

It is appreciated by those skilled in the art that the circuits, components, modules, and/or devices of, or associated with, the WIDQAS are described as being in signal communication with each other, where signal communication refers to any type of communication and/or connection between the circuits, components, modules, and/or devices that allows a circuit, component, module, and/or device to pass and/or receive signals and/or information from another circuit, component, module, and/or device. The communication and/or connection may be along any signal path between the circuits, components, modules, and/or devices that allows signals and/or information to pass from one circuit, component, module, and/or device to another and includes wireless or wired signal paths. The signal paths may be physical, such as, for example, conductive wires, electromagnetic wave guides, cables, attached and/or electromagnetic or mechanically coupled terminals, semi-conductive or dielectric materials or devices, or other similar physical connections or couplings. Additionally, signal paths may be non-physical such as free-space (in the case of electromagnetic propagation) or information paths through digital components where communication information is passed from one circuit, component, module, and/or device to another in varying digital formats without passing through a direct electromagnetic connection.

Each sensor may be a conventional sensor, for example, a conductivity sensor, humidity sensor, or both. Examples of the humidity sensor include a microelectromechanical systems ("MEMS") moisture sensor or a conventional humidity sensor. Examples of the conductivity sensor include a sensing probe such as, for example, a conductance probe and a pair of electrode structures that may be, for example, as simple as a pair of electrical wires. In this example, each electrode acts as a sensing element.

Specifically, in the example of a conductivity sensor, it is appreciated by those skilled in the art that a conductivity sensor is a sensor that is capable of measuring the electrical conductivity (also known as the specific conductance) of a material under test. Electrical conductivity (generally measured in Siemens per meter ("S/m")) is the reciprocal of electrical resistivity and as such measures the ability of the material to conduct an electric current.

In water specific applications, electrical conductivity measurements are well known to those skilled in the art and are routinely utilized a way of measuring the ionic content and impurity of a solution under test. In general, the electrical conductivity of a solution under test is measured by determining the resistance of the solution between two electrodes that are separated by a fixed distance and an alternating current is utilized in order to avoid electrolysis. The resistance is then measured by a conductivity meter. In operation, the power consumption to obtain the measurements may be minimal because typically only a very low resistive change would be needed to detect the presence of water at any given level for any given location. In general, the conductivity of a solution is highly temperature dependent as such conductivity measurements generally need to be calibrated to compensate for temperature effects.

Figure 3:
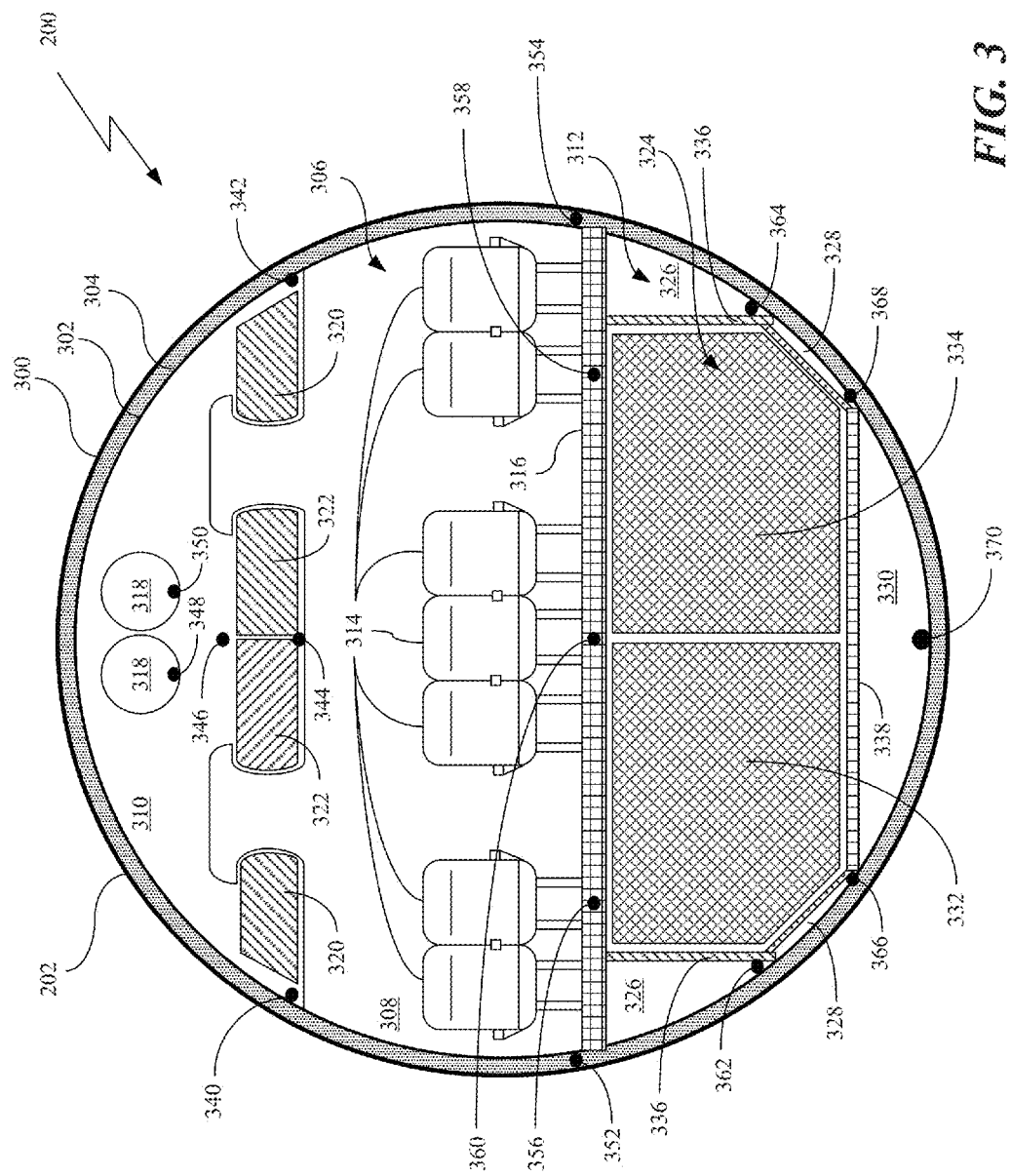
FIG. 3 is a front cross-sectional view of a cut-away portion of the fuselage of the airframe of the aircraft shown in FIG. 2 utilizing an example of an implementation of the WIDQAS in accordance with the present invention.

FIG. 3 is a front cross-sectional view of a cut-away portion of the fuselage 202 of the airframe of the aircraft 200 shown in FIG. 2 utilizing an example of an implementation of the WIDQAS in accordance with the present invention. The fuselage 202 includes outer fuselage skin 300, an inner fuselage skin 302, insulation blanket material 304, an upper lobe 306 of the airframe, a passenger cabin 308 within the upper lobe 306, a fuselage crown 310 above the passenger cabin 308, and a lower lobe 312 below the passenger cabin 308. The inner fuselage skin 302 may be composed of a plurality of interior panels. The passenger cabin 308 may include a plurality of passenger seats 314 and passenger cabin floor 316, which may include a plurality of support beams (not shown). The fuselage crown 310 may include ECS ducts 318, outboard overhead storage compartments 320, and inboard overhead storage compartments 322. The lower lobe 312 may include a plurality of enclosed spaces such as, for example, a cargo bay 324 (also known as a cargo hold or cargo area), upper-outside corner spaces 326, lower-outside corner spaces 328, and a bottom space 330. The cargo bay 324 is usually configured to accept two side-by-side transverse rows of LD-3 containers 332 and 334 or one LD-6 container (not shown). Generally, the cargo bay 324 is defined at the top by the passenger cabin floor 316, on the sides by side frames 336 that divide the cargo bay 322 from the upper-outside corner spaces 326 and the lower-outside corner spaces 328, and at the bottom by a cargo floor beam 338 above the bottom space 330. The side frames 336 are partially vertical and partially beveled to accommodate for the curved profile of the lower portion of the fuselage 202. In this example, the side frames 336 may divide the upper-outside corner spaces 326 from lower-outside corner spaces 328 so that each is an individual enclosed space. Alternatively, in this example, the side frame 336 may be open such that upper-outside corner spaces and lower-outside corner spaces are actually only two enclosed spaces instead of four.

In this example, a plurality of sensors 340, 342, 344, 346, 348, 350, 352, 354, 356, 358, 360, 362, 364, 366, 368, and 370 may be located throughout the illustrated portion of the fuselage 202. Specifically, sensors 340 and 342 may be located in the fuselage crown 310 behind the outboard overhead storage compartments 320 next to the inner fuselage skin 302. Sensors 344 and 346 may be located in the fuselage crown 310 below and above the inboard overhead storage compartments 322, respectively. Sensors 348 and 350 may be located in the fuselage crown 310 within, or below, the ECS ducts 318. Sensors 352 and 354 may be located between the outer fuselage skin 300 and inner fuselage skin 302, in the insulation blanket material 304, at a location that is approximately at the level of the passenger cabin floor 316. Sensors 356, 358, and 360 may be located at points along the surface of, or within, the passenger cabin floor 316. Sensors 362 and 364 may be located in the lower lobe 312 at the bottom of the upper-outside corner spaces 326 and sensors 366 and 368 may be located in the lower lobe 312 at the bottom of the lower-outside corner spaces 328. Finally, sensor 370 may be located in the lower lobe 312 at the bottom of the bottom space 330.

In general, the locations of the plurality of sensors are determined from either locations that are known to have water ingress, condensation, or accumulation problems, or locations that are believed to possibly have these problems. In general, these locations may be built into the aircraft 200 during fabrication or added later as water related data is measured and analyzed. If added later, the locations may change based on the accumulation of historical data regarding this specific aircraft 200 and/or data regarding a plurality of other aircraft that is of the same type. Moreover, by monitoring the plurality of sensors in these different locations the aircraft operators, maintenance crews, and designers may utilize the recorded measurement data to monitor operation of the aircraft, maintenance of components in the aircraft, and determine possible improvements in the design of the aircraft, respectively.

Specifically, aircraft operators may utilize the WIDQAS to monitor the ingress of water into the aircraft 200, determine the humidity in certain areas in the aircraft (generally areas that are defined as enclosed spaces), determine if water is condensing and turning to ice in important areas of the aircraft (for example, water freezing in places where there are mechanical actuators, such as, doors, window shade units, servo areas, control surfaces, landing gear, etc.), and determine whether water is accumulating in certain areas close to important electrical and/or electronic equipment and wiring. This process may be accomplished in real-time so that the air crew operating the aircraft is aware of any potential problems caused by water and ice. As for the maintenance crews, the historical data generated by the WIDQAS allows the maintenance crews to determine which parts of the aircraft 200 seem to be exhibiting the most water ingress (for example, the doors in the passenger cabin or cargo bay), which parts of the aircraft 200 are experiencing out-of-the-ordinary humidity levels, which areas are experiencing condensation and freezing, and which areas are experiencing accumulating water. As an example, using the historical data generated by the WIDQAS, the maintenance crews may remove any accumulated water in the aircraft 200 at the different enclosed spaces (that are being monitored by the WIDQAS), check for corrosion in the monitored areas of the aircraft 200, replace parts that have been damaged (such as electrical or electronic systems and wires or wire harnesses) or that have had accumulated a predetermined amount of water (such as, for example, parts of the insulation blanket material 304), place additional insulation in areas that are prone to ice (i.e., such as frost) formation, replace parts that have been damaged by ice (such as, for example, mechanical actuated parts or systems), place drainage holes or other drainage systems in the spaces that are accumulating water, and store the measurement data from the aircraft 200 for use in monitoring and maintaining other similar aircraft and/or other aircraft flying through the same flight paths. Moreover, aircraft manufactures may utilize the measurement data for future use in installing drainage systems (such as, for example, drainage holes or other types of drainage schemes) in future production units of the aircraft type, redesigning some of the enclosed spaces to minimize condensation or ice formation, and installing additional sensors and data measurement devices throughout future production units of the aircraft type. Additionally, aircraft manufactures may utilize the measurement data for improving future production models and designs.

Turning to FIG. 4A, in FIG. 4A, a front cross-sectional view of a cut-away portion of an enclosed space (in this example, the upper-outside corner space 326 shown in FIG. 3) utilizing an example of an implementation of the WIDQAS in accordance with the present invention. In this example, only the inside of upper-outside corner space 326 is shown and the enclosed space of the upper-outside corner space 326 is defined by the inner fuselage skin 302, passenger cabin floor 316, and side frame 336. For purposes of illustration, the upper-outside corner space 326 in this example is shown as isolated (at least somewhat) from the lower-outside corner space 328 (of FIG. 3) so as to illustrate the creation of an accumulated water pool 400 having a water level 402. In this example, the sensor 362 in FIG. 3 may be three sensors 404, 406, and 408 arranged along the inner fuselage skin 302 for measuring the height of water level 402 that corresponds to the amount of water accumulation within the accumulated water pool 400. The three sensors 404, 406, and 408 may be conductivity sensors arranged such that the second sensor 406 may be a predetermined distance 409 above the height of the first sensor 404 and the third sensor may be another predetermined distance 411 above the height of the second sensor 406. As an example, the two predetermined distances 409 and 411 may be approximately equal to 0.125 inches.

In this example, the water level 402 height of the accumulated water pool 400 is shown to be above the height of the first sensor 404, but below the heights of the second 406 and third 408 sensors. As such, the first sensor 404 would detect the presence of the water and pass that information to the data measurement device that there is water accumulation present in the upper-outside corner space 326. However, since only the first sensor 404 detects the presence of water, the data measurement device knows that the water level 402 is at a first level (such as, a level "A"). If the second sensor 406 also detects the presence of water, but not the third sensor 406, then the data measurement device knows that the water level 402 is at a second level (such as, a level "B"). Finally, if the third sensor 408 also detects the presence of water, then the data measurement device knows that the water level 402 has reached a third level (such as, a level "C"). Once, all three sensors 404, 406, and 408 have detected water, the accumulated water may continue to increase such that the water level will continue to rise past the height of the third sensor 408. At this point the only way to know what the water level 402 is at any point in time after the third sensor 408 initially detects the presence of water is to either add more sensors (not shown) at higher levels or to utilize a prediction model that takes into account past measurements in the upper-outside corner space 326 and can predict the rate of accumulation of water in the accumulated water pool 400. Again, in this example, it is assumed that the accumulated water pool 400 does not drain (at least significantly) into the lower-outside corner space 328 (FIG. 3). In this example, based on the conductivity measurements made by the first, second and third sensors 404, 406, and 408, the data measurement device may be able to determine not only the water level 402 of the accumulated pool of water 400 but also the purity of the water in the accumulated pool of water 400. As an example, if the upper-outside corner space 326 is near a toilet or waste pipe, a fuel line, or hydraulic line, the sensors 404, 406, and 408 may be utilized to determine if there has been any leakage from the toilet, waste pipe, fuel line, or hydraulic line. Any leakage from these systems will cause impurities in the accumulated pool of water 400 that may be detected by the sensors 404, 406, and 408 via conductivity measurements.

In FIG. 4B, a side cross-sectional view of an enlarged portion of the cut-away portion 413 of the enclosed space shown in FIGS. 3 and 4A utilizing an example of an implementation of the WIDQAS in accordance with the present invention is shown. Specifically, FIG. 4B is a cross-sectional view of an enlarged portion of the cut-away portion 413 along cutting plane A-A' 410 looking into the inner fuselage skin 302. In this example, the first sensor 404 may include a first electrode 412 and second electrode 414, the second sensor 406 may include a first electrode 416 and second electrode 418, and the third sensor 408 may include a first electrode 420 and second electrode 422. The first electrodes 412, 416, and 420 may be spaced a distance 424 apart from the second electrodes 414, 418, and 422, respectively. The distance 424 is predetermined so as to optimize the conductivity measurement between the first electrodes 412, 416, and 420 and second electrodes 414, 418, and 422. An example distance 424 may be equal to approximately 1 to 6 inch(es) in length. This distance 424 may be determined by the type of conductivity probes utilized and the distance 424 that they may be apart and still allow for a meaningful conductivity measurement. It is appreciated that in certain applications and at a certain small distance 424, the electrodes 412, 414, 416, 418, 420, and 422 may be simply the conductor ends of the corresponding wires 432, 434, 436, 438, 440, and 442, respectively. These conductor ends may be small metallic flat plates, metallic bulbs, or simple exposed wire.

In an example of operation, the first electrode 412 of the first sensor 404 may attempt to drive a first current 426 to the second electrode 414. Similarly, the first electrode 416 of the second sensor 406 may attempt to drive a second current 428 to the second electrode 418 and the first electrode 420 of the third sensor 408 may attempt to drive a third current 430 to the second electrode 422. Since in this example only the first electrode 412 and the second electrode 414 of the first sensor 404 are under the water level 402 of the accumulated water pool 400, only first electrode 412 and second electrode 414 will be in signal communication via first current 426 and, therefore, only the first sensor 404 will detect the presence of water and produce a conductivity measurement value for the accumulated water pool 400. In this example, it is appreciated that the first electrodes 412, 416, and 420 and second electrodes 414, 418, and 422 are shown being in signal communication with the data measurement device or devices via the plurality of wires 432, 436, 440, 434, 438, and 442, respectively.

Figures 5A, 5B:
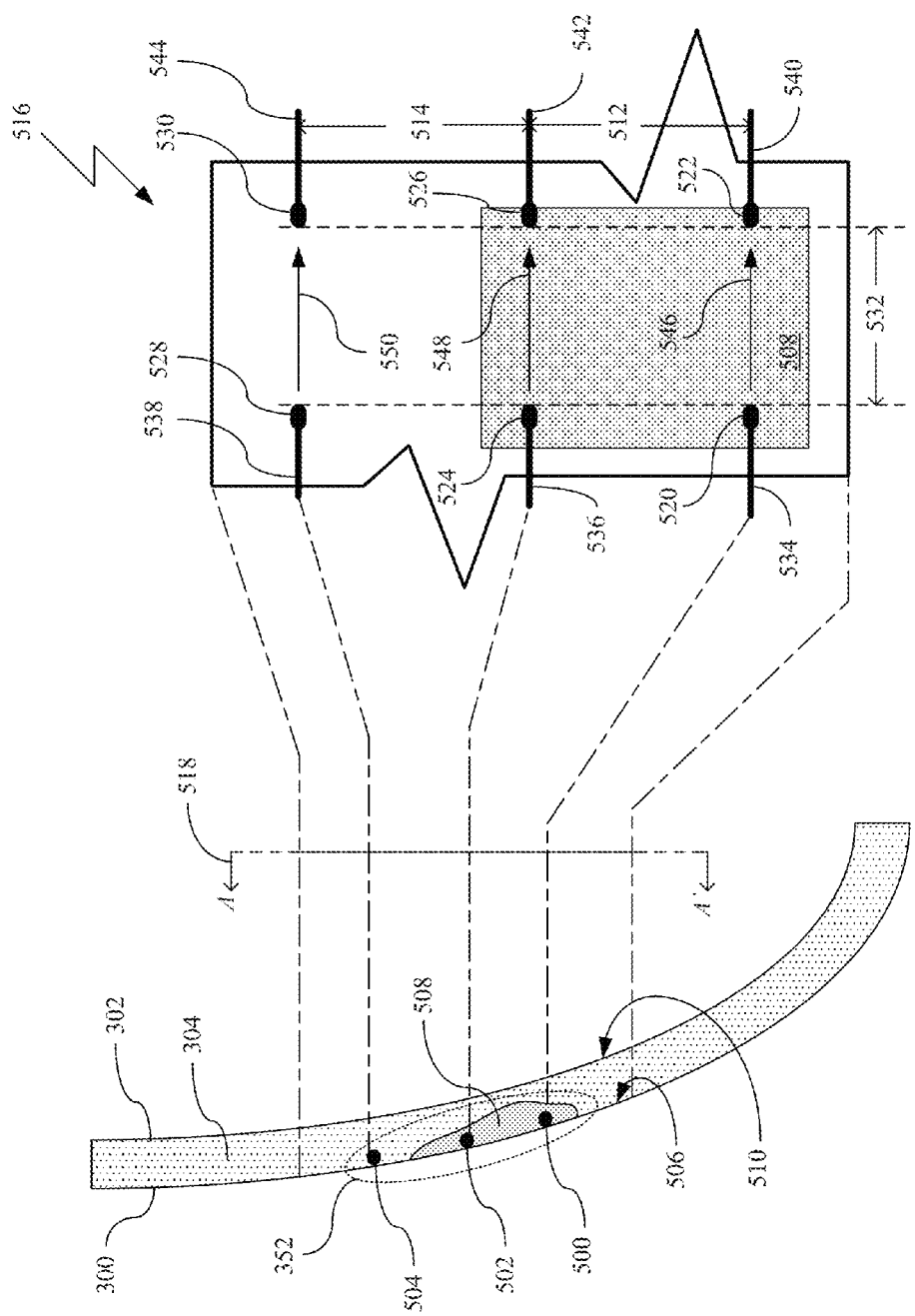
FIG. 5A is a front cross-sectional view of a cut-away portion of another enclosed space shown in FIG. 3 utilizing another example of an implementation of the WIDQAS in accordance with the present invention.
FIG. 5B is a side cross-sectional view of an enlarged portion of the cut-away portion of the enclosed space shown in FIGS. 3 and 5A utilizing an example of an implementation of the WIDQAS in accordance with the present invention.

In FIG. 5A, a front cross-sectional view of a cut-away portion of another enclosed space shown in FIG. 3 utilizing another example of an implementation of the WIDQAS in accordance with the present invention is shown. In this example, for illustration purposes, only the outer fuselage skin 300, an inner fuselage skin 302, and insulation blanket material 304 is shown. Similar to the description related to FIG. 4A, this example, the sensor 352 (in FIG. 3) is shown to actually be three sensors 500, 502, and 504 arranged along the surface 506 of the outer fuselage skin 300 for measuring the presence and size of ice 508 formed on the inner surface 506 (such an accumulation of frost) between the outer fuselage skin 300 and the inner fuselage skin 302 along the insulation blanket material 304. Alternatively, it is appreciated that if the insulation blanket material 304 does not significantly reduce the temperature of the inner fuselage skin 302 in relation to the temperature of the outer fuselage skin 300, the inner fuselage skin 302 may also be a temperature that is below the freezing point of water and the ice may actually form on the inner surface 510 of the inner fuselage skin 302. In this other example, three additional sensors (not shown but similar to sensors 500, 502, and 504) may be arranged along the inner surface 510 of the inner fuselage skin 302 for measuring the presence and size of ice 506 formed on the inner surface 510.

Similar to the example described in FIG. 4A, the three sensors 500, 502, and 504 may be conductivity sensors arranged such that the second sensor 502 may be a predetermined distance 512 above the height of the first sensor 500 and the third sensor 504 may be another predetermined distance 514 above the height of the second sensor 502. As an example, the two predetermined distances 512 and 514 may be approximately equal to 0.125 inches.

In this example, the size of the ice 508 is shown to extend beyond the position of the first sensor 500 and second sensor 502 but not to the position of the third sensor 504. As such, the first sensor 500 and second sensor 502 will detect the presence of the water in the form of ice 508 and pass that information to the data measurement device that there is ice 508 present on the inner surface 506 at the positions of the first and sensors 500 and 502. In this example, if the first sensor 500 represents a first level (such as, a level "A"), the second sensor 502 a second level (such as, a level "B"), and the third sensor 504 a third level (such as, a level "C"), then the data measurement device knows that the ice 508 extends from level A to level B but not level C.

Once all three sensors 500, 502, and 504 have detected the ice 508, the size of the ice 508 may continue to increase such that at that point the only way to know how much ice 508 there is at any point in time after all three sensors 500, 502, and 504 initially detect the ice 508 is to either add more sensors (not shown) at distances farther apart from the middle sensor (i.e., second sensor 502) or to utilize a prediction model that takes into account past measurements and can predict the rate of ice 508 growth (i.e., formation of frost) along the inner surface 506 of the outer fuselage skin 300.

In FIG. 5B, a side cross-sectional view of an enlarged portion of the cut-away portion 516 of the enclosed space shown in FIGS. 3 and 5A utilizing an example of an implementation of the WIDQAS in accordance with the present invention is shown. Specifically, FIG. 5B is a cross-sectional view of an enlarged portion of the cut-away portion 516 along cutting plane A-A' 518 looking into the inner surface 506 of the outer fuselage skin 300. In this example, the first sensor 500 may include a first electrode 520 and second electrode 522, the second sensor 502 may include a first electrode 524 and second electrode 526, and the third sensor 504 may include a first electrode 528 and second electrode 530. The first electrodes 520, 524, and 528 may be spaced a distance 532 apart from the second electrodes 522, 524, and 530, respectively. As described before, the distance 532 is predetermined so as to optimize the conductivity measurement between the first electrodes 520, 524, and 528 and second electrodes 522, 524, and 530, respectively. An example distance 532 may be equal to approximately 1 to 6 inch(es) in length. This distance 532 may be determined by the type of conductivity probes utilized and the distance 532 that they may be apart and still allow for a meaningful conductivity measurement. It is appreciated that in certain applications and at a certain small distance 532, the electrodes 520, 522, 524, 526, 528, and 530 may be simply the conductor ends of the corresponding wires 534, 540, 536, 542, 538, and 544, respectively. These conductor ends may be small metallic flat plates, metallic bulbs, or simple exposed wire.

In an example of operation, the first electrode 520 of the first sensor 500 may attempt to drive a first current 546 to the second electrode 522. Similarly, the first electrode 524 of the second sensor 502 may attempt to drive a second current 548 to the second electrode 526 and the first electrode 528 of the third sensor 504 may attempt to drive a third current 550 to the second electrode 530. Since in this example only the first electrodes 520 and 524 and the second electrodes 522 and 526 are within the ice 508, only first electrodes 520 and 524 and the second electrodes 522 and 526 will be in signal communication via first current 546 and second current 548, respectively, and, therefore, only the first and second sensors 500 and 502 will detect the presence of ice 508 and produce a conductivity measurement value for the ice 508. In this example, it is appreciated that the first electrodes 520, 524, and 528 and the second electrodes 522, 526, and 530 are shown being in signal communication with the data measurement device or devices via the plurality of wires 534, 536, 538, 540, 542, and 544, respectively.

Figure 6:
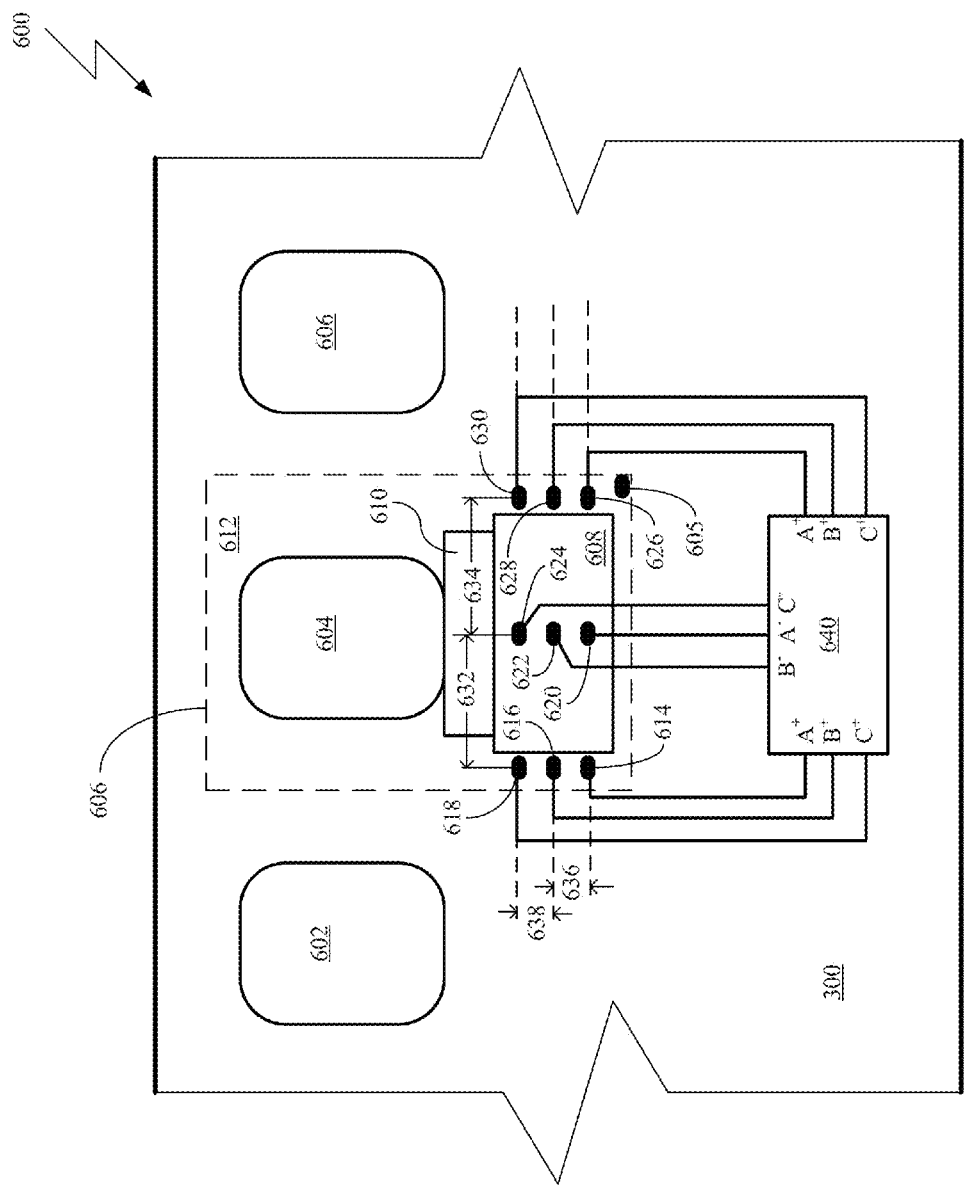
FIG. 6 is a side view of a portion of the fuselage of the airframe of the aircraft shown in FIG. 2 utilizing another example of an implementation of the WIDQAS in accordance with the present invention.

In FIG. 6, a side view of a portion 600 of the fuselage 202 of the airframe of the aircraft shown in FIG. 2 utilizing another example of an implementation of the WIDQAS in accordance with the present invention is shown. In this example, three windows 602, 604, and 606 are shown along portion 600 of the fuselage 202, where the second window 604 is shown in a cut-out view 606 cut into the outer fuselage skin 300. The cut-out view 606 shows a window shade mechanism 608 having a window shade 610 that rises to cover the second window 604 and drainage hole 605. As described earlier, water may accumulate in the enclosed space 612 were the window shade mechanism 608 is located. To detect this accumulation of water, sensors 614, 616, 618, 620, 622, 624, 626, 628, and 630 may be located throughout the enclosed space 612 to detect the presence of, and accumulation of, water. Similar to the examples in FIGS. 4A, 4B, 5A, and 5B, the sensors 614, 616, 618, 620, 622, 624, 626, 628, and 630 may be conductivity sensors where each conductivity sensor 614, 616, 618, 620, 622, 624, 626, 628, and 630 is an electrode. In this example, the first column of sensors 614, 616, and 618 may be spaced apart a first predetermined distance 632 from the second column of sensors 620, 622, and 624. Similarly, the third column of sensors 626, 628, and 630 may be spaced apart a second predetermined distance 634 from the second column of sensors 620, 622, and 624. As an example, the first and second predetermined distances 632 and 634 may be approximately about 6 to 8 inches. Additionally, the first row of sensors 614, 620, and 626 may be spaced apart a first predetermined distance 636 from the second row of sensors 616, 622, and 628 and the third row of sensors 618, 624, and 630 may be spaced apart a second predetermined distance 638 from the second row of sensors 616, 622, and 628. In this example, the first and second predetermined distances 636 and 638 may be approximately 0.125 inches.

In this example, the sensors 614, 616, 618, 620, 622, 624, 626, 628, and 630 may be conductivity sensors that are in signal communication with a conductivity meter 640 that measures the conductivity between the respective sensors. The conductivity meter 640 is in signal communication with the data measurement device (not shown). Specifically, if the electrodes 620, 622, and 624 are negative electrodes and the electrodes 614, 616, 618, 626, 628, and 630 are positive electrodes, then the conductivity meter 640 is configured to measure the conductivity between the electrodes 614 and 620 (i.e., conductivity between $A^+$ and $A^-$), 626 and 620 (i.e., conductivity between $A^+$ and $A^-$), 616 and 622 (i.e., conductivity between $B^+$ and $B^-$), 628 and 622 (i.e., conductivity between $B^+$ and $B^-$), 618 and 624 (i.e., conductivity between $C^+$ and $C^-$), and 630 and 624 (i.e., conductivity between $C^+$ and $C^-$). The resulting values are then passed to the data measurement device (not shown).

Figure 7:
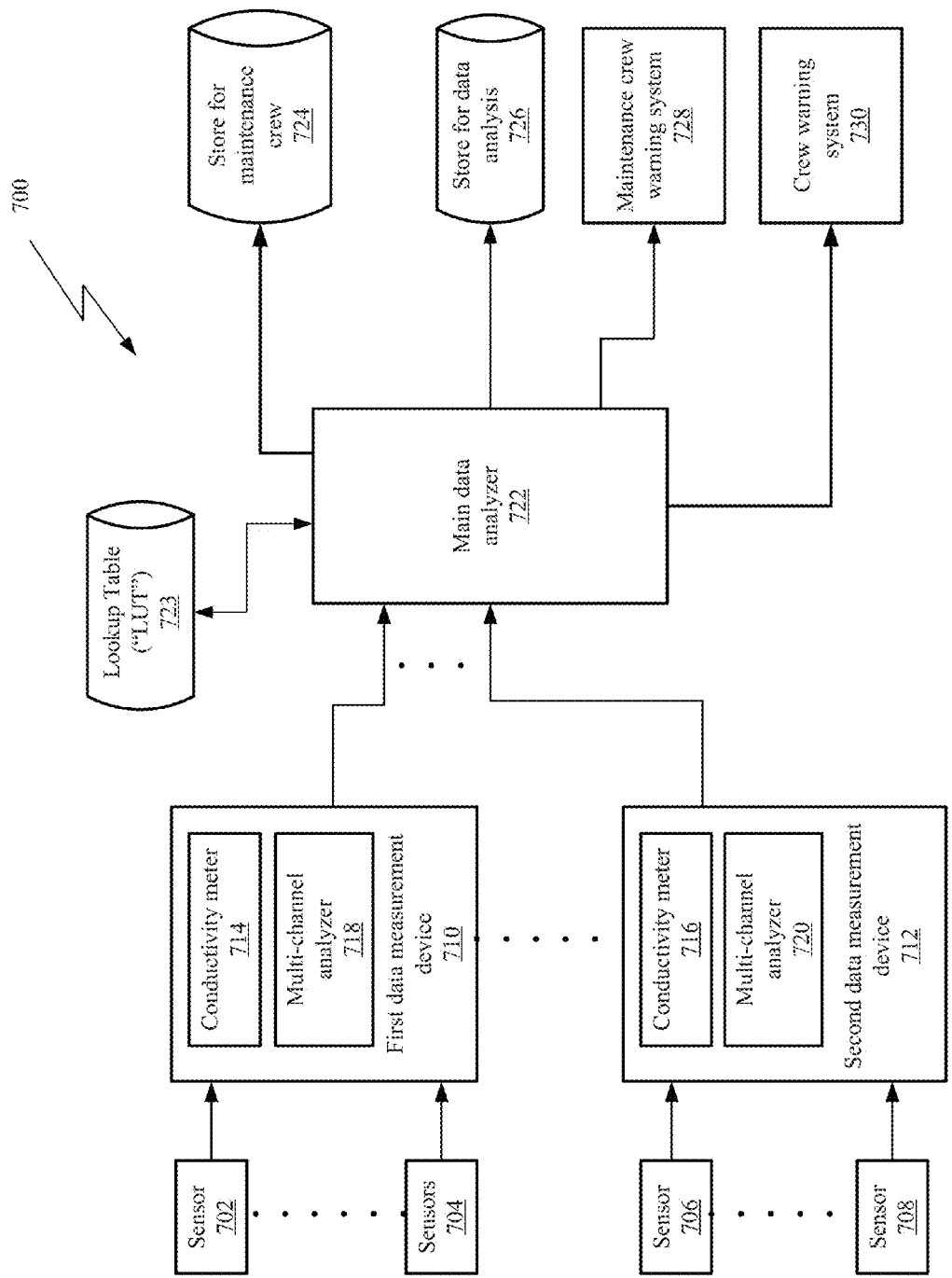
FIG. 7 is a block diagram of an example of an implementation of the WIDQAS for use with the aircraft described in FIGS. 2 through 6, in accordance with the present invention.

In FIG. 7, a block diagram of an example of an implementation of the WIDQAS 700 for use with the aircraft described in FIGS. 2 through 6, in accordance with the present invention, is shown. As described earlier, the WIDQAS 700 may include a plurality of sensors 702, 704, 706, and 708 that are located throughout the aircraft 200 usually within separate enclosed spaces (not shown in FIG. 7 but described in the previous description and associated figures). In this example, sensors 702 and 704 are in signal communication with a first data measurement device 710 and sensors 706 and 708 are in signal communication with a second data measurement device 712. It is noted that while only two data measurement devices 710 and 712 and two sensor pairs 702 and 704, and 706 and 708, corresponding to the two data measurement devices 710 and 712, respectively, are shown, this is for illustrative purposes only. As described earlier, there may be a large plurality of sensors located throughout the aircraft 200 and this plurality of sensors may be divided into sub-pluralities of sensors where each sub-plurality of sensors is associated with a single data measurement device. Each data measurement device may include a plurality of channels corresponding to the sub-plurality of sensor. Moreover, there may be a plurality of data measurement devices located either in a proximity to each other or throughout the aircraft 200 near the location of the sub-plurality of sensors corresponding to the individual data measurement device.

As an example, each data measurement device 710 and 712 may include a conductivity measurement device (such as, for example, a conductivity meter) 714 and 716 and a multi-channel analyzer 718 and 720. The plurality of data measurement devices 710 and 712 may be in signal communication with a main data analyzer 722. The main data analyzer 722 may be a processor based device capable of receiving the data from the plurality of data measurement devices 710 and 712, organizing the data, storing it based on certain criteria, and communicating with the aircraft 200 crew and/or ground maintenance crews. The main data analyzer 722 may act as a data recorder that receives all the information from the data measurement devices 710 and 712 and organizes it as needed. In general, the main data analyzer 722 will include at least one processor capable of being programmed with software. Similarly, each data measurement device 710 and 712 may also be a processor based device capable of being programmed with software, a digital signal processor ("DSP"), application specific integrated circuit ("ASIC"), or field programmable gate array ("FPGA").

As an example of operation, the main data analyzer 722 may make use of a lookup table ("LUT") on a storage device 723 in signal communication with the main data analyzer 722. The LUT may have preprogrammed values that when compared to the measured values from the data measurement devices 710 and 712, can be used to trigger other actions such as notifications of the aircraft 200 crew and/or maintenance crews on the ground. The LUT may also provide the main data analyzer 722 with additional information related to how the main data analyzer 722 may store the acquired measured data from the data measurement devices 710 and 712 for either the maintenance crews or for further data analysis.

The main data analyzer 722 may store the data acquired throughout the flight to a first database 724 for the maintenance crew. Additionally, the main data analyzer 722 may also store the data acquired throughout the flight to a second database 726 for the data analysis at a later time. Moreover, the main data analyzer 722 is configured to communicate with a crew warning system 730 to notify the crew of a high priority problem. Similarly, the main data analyzer 722 is also configured to communicate with a ground maintenance crew warning system 728 to notify the maintenance crew on the ground of a lower level problem that requires attention once the aircraft 200 has landed.

It is appreciated that the data measurements may be collected in real-time or over the duration of a flight. Additional information may be stored with the actual data measurements. For example, a time stamp, temperature, and other pertinent information may be stored with each data measurement, which may be utilized to map the accumulation of water and the transition of water to ice during a given flight. The data collected may be used to map the presence of water in the monitored locations in the aircraft 200 and at various times during the flight.

Figure 8:
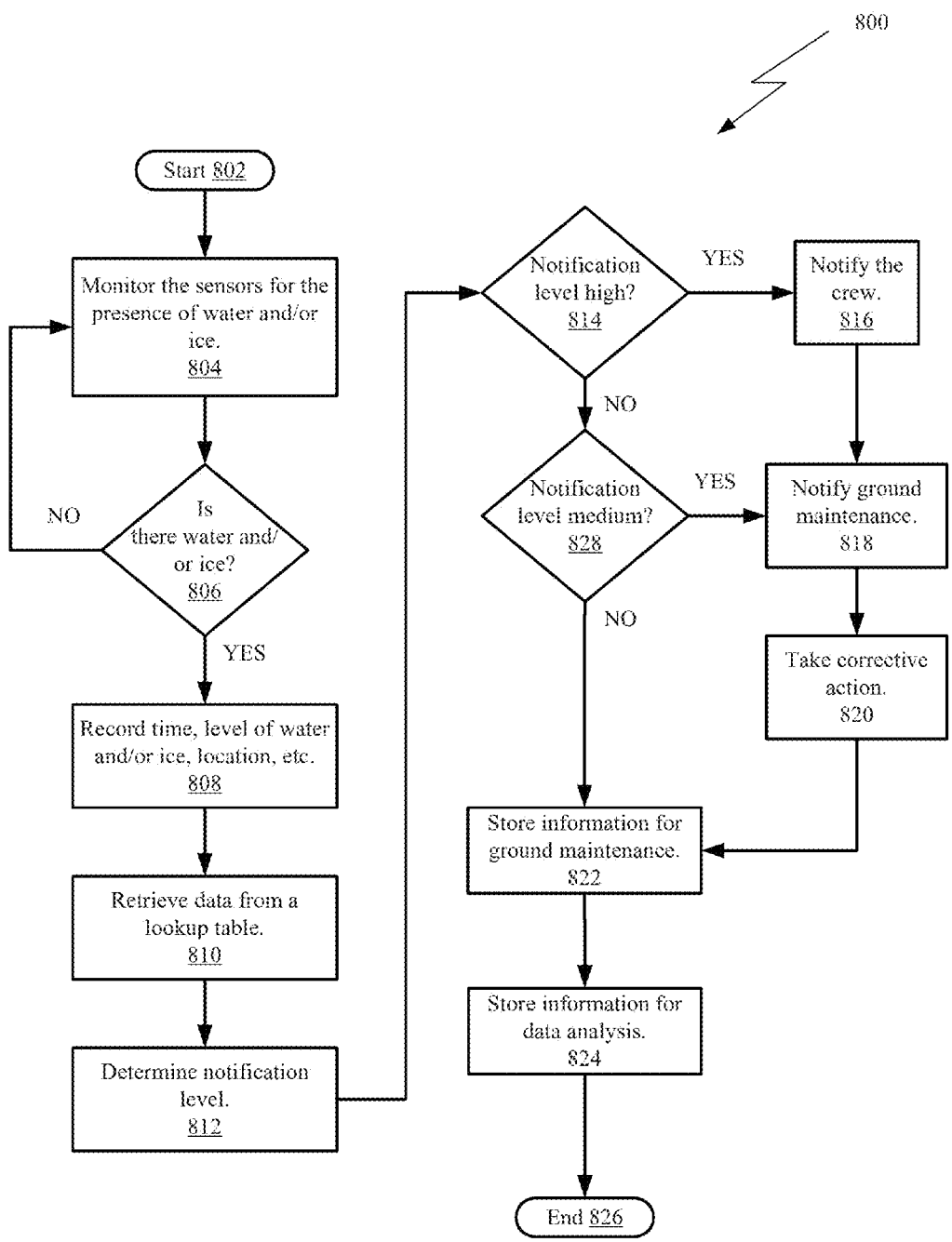
FIG. 8 is a flowchart of an example of an implementation of a process performed by the WIDQAS shown in FIGS. 2 through 7 in accordance with the present invention.

In FIG. 8, a flowchart 800 of an example of an implementation of a process performed by the WIDQAS shown in FIGS. 2 through 7 in accordance with the present invention is shown. The process begins 802 and at step 804, the WIDQAS monitors the sensors for the presence of water and/or ice in any of the locations where the sensors are located (as described previously). In decision step 806, if there is no detection of water and/or ice in any of the locations the process repeats at step 804. If instead, there is a detection of water and/or ice, the process continues to step 808. In step 808, the WIDQAS records identifying information such as, for example, time, level of water, size of ice, location of the detection, etc. The WIDQAS then retrieves data, in step 810, from the LUT to determine how to process, store, and/or communicate the measured data. If the WIDQAS determines that the measured data needs to be communicated to either the aircraft crew or maintenance crew on the ground, the WIDQAS first determines, in step 812, the level of importance for the notification.

If the notification level is high, then in decision step 814, the WIDQAS either directly, or through another system in signal communication with the WIDQAS, notifies the flight crew of the aircraft 200 in step 816. Generally, this notification will also be sent to the ground maintenance crew on the ground in step 818. The WIDQAS may then take any corrective action that is directed by the flight crew, in step 820. The measured data and the corrective action taken by the flight crew may then be stored on a storage unit (i.e., a memory unit) in step 822 for use by the maintenance crew on the ground. The same information may also be stored, in step 824, in a separate storage unit for use in future data analysis. The process then ends 826.

If instead, the notification is not high but medium, then in decision step 814, the WIDQAS either directly, or through another system in signal communication with the WIDQAS, notifies the ground maintenance crew on the ground in step 818 but not the flight crew. The WIDQAS may then take any corrective action that is directed by the ground maintenance crew, in step 820. The measured data and the corrective action taken may then be stored on the storage unit in step 822 for use by the maintenance crew on the ground. The same information may also be stored, in step 824, in the separate storage unit for use in future data analysis. The process then again ends 826.

Moreover, if it is determined that there is no need for notifying either the flight crew or ground maintenance crew, in decision steps 814 and 828, the WIDQAS then stores the measured data on the storage unit in step 822 for use by the maintenance crew on the ground. The same information may also be stored, in step 824, in the separate storage unit for use in future data analysis. The process then again ends 826.

It will be understood that various aspects or details of the invention may be changed without departing from the scope of the invention. It is not exhaustive and does not limit the claimed inventions to the precise form disclosed. Furthermore, the foregoing description is for the purpose of illustration only, and not for the purpose of limitation. Modifications and variations are possible in light of the above description or may be acquired from practicing the invention. The claims and their equivalents define the scope of the invention.

What is claimed is:

1. A water and ice detection and quantitative assessment system ("WIDQAS") for moisture detection and assessment of water accumulation on an aircraft having an airframe that has at least one enclosed space within the airframe, the WIDQAS comprising:
   a plurality of sensors arranged in the at least one enclosed space within the airframe,
      wherein each sensor of the plurality of sensors is configured to detect a presence of moisture in the at least one enclosed space and generate a data measurement that is responsive to the detection of moisture in the at least one enclosed space,
      wherein the plurality of sensors includes a plurality of conductivity sensors, each conductivity sensor of the plurality of conductivity sensors includes a first electrode and a second electrode spaced apart from the first electrode, and the first and the second sensing electrodes are configured to detect the presence of moisture,
      wherein the plurality of sensors further includes a first sensing element and a second sensing element, and the first sensing element is configured to detect a first amount of moisture accumulation and the second sensing element is configured to detect a second amount of moisture accumulation that is greater than the first amount of moisture accumulation; and
   a data measurement device in signal communication with the plurality of sensors,
      wherein the data measurement device is configured to record the data measurement for each sensor, and the data measurement device is configured to record identifying information about the data measurement during a flight of the aircraft.

2. The WIDQAS of claim 1, wherein the data measurement device includes a multi-channel analyzer.

3. The WIDQAS of claim 2, wherein the data measurement device includes a conductivity meter.

4. The WIDQAS of claim 2, further including a main data analyzer in signal communication with the data measurement device.

5. The WIDQAS of claim 4, further including a second data measurement device in signal communication with the main data analyzer and a second plurality of sensors.

6. The WIDQAS of claim 5, further including a storage device for storing the data measurement and the identifying information.

7. The WIDQAS of claim 6, wherein the identifying information includes a time of the detection in the enclosed space, a level of water, a size of ice, and a location of the detection in the enclosed space.

8. The WIDQAS of claim 7, further including a communication device in signal communication with the main data analyzer, wherein the communication device is configured to notify a flight crew of the aircraft.

9. The WIDQAS of claim 8, further including another storage device having data organized in a lookup table ("LUT"), wherein the main data analyzer is configured to utilize the LUT in storing the data measurement and the identifying information and for determining a notification level for notifying the flight crew.

10. A method for moisture detection and assessment of water accumulation on an aircraft having an airframe, utilizing a water and ice detection and quantitative assessment system ("WIDQAS") having a plurality of sensors arranged in at least one enclosed space within the airframe, the method comprising:
monitoring the plurality of sensors for the presence of moisture in the at least one enclosed space, wherein each sensor of the plurality of sensors is configured to detect a presence of moisture in the at least one enclosed space and generate a data measurement that is responsive to the detection of moisture in the at least one enclosed space,
wherein monitoring the plurality of sensors includes monitoring a plurality of conductivity sensors, wherein each conductivity sensor of the plurality of conductivity sensors includes a first electrode and a second electrode spaced apart from the first electrode, and the first and the second sensing electrodes are configured to detect the presence of moisture, and
wherein monitoring the plurality of sensors further includes monitoring a first sensing element and a second sensing element, and wherein the first sensing element is configured to detect a first amount of moisture accumulation and the second sensing element is configured to detect a second amount of moisture accumulation that is greater than the first amount of moisture accumulation;
receiving the data measurement indicating the presence of moisture at a sensor of the plurality of sensors;
recording identifying information related to the sensor;
retrieving data from a lookup table ("LUT"), wherein the LUT data is related to the sensor;
determining a notification level for the received data measurement from the sensor using the LUT data; and
storing the received data measurement with the corresponding identifying information on a storage device.

11. The method of claim 10, wherein the identifying information includes a time of the detection in the enclosed space, a level of water, a size of ice, and a location of the detection in the enclosed space.

12. The method of claim 11, further including notifying a flight crew of the aircraft of the received data measurement in response to determining that the notification level is of a high priority.

13. The method of claim 12, further including notifying a maintenance crew of the received data measurement in response to determining that the notification level is medium.

14. The method of claim 11, wherein storing the received data measurement includes storing the received data measurement for further data analysis.

15. The method of claim 11, wherein the method is performed in real-time.

16. The method of claim 11,
wherein monitoring the plurality of sensors for the presence of water includes monitoring the plurality of sensors for the presence of ice, and
wherein receiving a data measurement indicating the presence of water at a sensor of the plurality of sensors includes receiving a data measurement indicating the presence of ice at a sensor of the plurality of sensors.

17. A water and ice detection and quantitative assessment system ("WIDQAS") for moisture detection and assessment of water accumulation on an aircraft having an airframe that has at least one enclosed space within the airframe, the WIDQAS comprising:
a plurality of sensors arranged in the at least one enclosed space within the airframe,
wherein each sensor of the plurality of sensors includes a means for detecting a presence of moisture in the at least one enclosed space and generate a data measurement that is responsive to the detection of moisture in the at least one enclosed space,
wherein the plurality of sensors includes a plurality of conductivity sensors, each conductivity sensor of the plurality of conductivity sensors includes a first electrode and a second electrode spaced apart from the first electrode, and the means for detecting the presence of moisture includes the first and the second sensing electrodes configured to detect the presence of moisture, and
wherein the plurality of sensors further includes a first sensing element and a second sensing element, and the first sensing element is configured to detect a first amount of moisture accumulation and the second sensing element is configured to detect a second amount of moisture accumulation that is greater than the first amount of moisture accumulation; and
a data measurement device in signal communication with the plurality of sensors,
wherein the data measurement device includes a means for recording the data measurement for each sensor, and
wherein the data measurement device includes a means for recording identifying information about the data measurement during a flight of the aircraft.

18. The WIDQAS of claim 17, wherein the data measurement device includes a multi-channel analyzer.

19. The WIDQAS of claim 18, wherein the data measurement device includes a conductivity meter.

20. The WIDQAS of claim 18, further including a main data analyzer in signal communication with the data measurement device.

* * * * *